(12) United States Patent
Spangenburg et al.

(10) Patent No.: US 10,487,302 B2
(45) Date of Patent: Nov. 26, 2019

(54) METHODS AND APPARATUSES FOR CULTIVATING PHOTOTROPIC MICROORGANISMS

(71) Applicant: NSE, Inc., Santa Fe, NM (US)

(72) Inventors: Luke Spangenburg, Santa Fe, NM (US); Charles J Call, Albuquerque, NM (US)

(73) Assignee: NSE, Inc., Santa Fe, NM (US)

( * ) Notice: Subject to any disclaimer, the term of this patent is extended or adjusted under 35 U.S.C. 154(b) by 0 days.

(21) Appl. No.: 14/698,661

(22) Filed: Apr. 28, 2015

(65) Prior Publication Data

US 2015/0247111 A1    Sep. 3, 2015

Related U.S. Application Data

(63) Continuation-in-part of application No. 13/872,084, filed on Apr. 27, 2013, now abandoned.
(Continued)

(51) Int. Cl.
*C12M 3/00* (2006.01)
*C12M 1/00* (2006.01)
(Continued)

(52) U.S. Cl.
CPC ........... *C12M 21/02* (2013.01); *C12M 23/06* (2013.01); *C12M 37/00* (2013.01); *C12M 41/12* (2013.01);
(Continued)

(58) Field of Classification Search
CPC ...... C12M 21/02; C12M 41/12; C12M 41/18; C12M 43/04
See application file for complete search history.

(56) References Cited

U.S. PATENT DOCUMENTS

| | | | | | |
|---|---|---|---|---|---|
| 2,732,663 | A | * | 1/1956 | Dewey | A01G 33/00 47/1.4 |
| 4,287,876 | A | * | 9/1981 | Jacques | F24S 80/30 126/624 |
| 4,922,720 | A | * | 5/1990 | Finn | F03G 6/005 60/641.8 |
| 2005/0126559 | A1 | * | 6/2005 | Cleef | E04H 4/103 126/561 |

(Continued)

OTHER PUBLICATIONS

Masojidek et al., J. Appl. Phycol., 2009, vol. 21, p. 55-63.*
Masojidek et al., J. Appl. Phycol., 2009, vol. 21, p. 55-63 (Year: 2009).*

*Primary Examiner* — Nathan A Bowers
(74) *Attorney, Agent, or Firm* — ipTekk, LLC; Anand S. Chellappa

(57) ABSTRACT

Method and apparatus for biomass cultivation (preferably using algae) incorporating photo bio-reactor (PBR) technology coupled with a heat sink to increase energy efficiency. An external PBR array is coupled to an indoor storage tank system with a volume equal to or greater than the volume of the PBR array. A controller can be used to optimize the growth of biomass by optimizing three key growth parameters: exposure to sunlight, temperature and nutrients. The indoor tank system serves as a reservoir where algae can be protected from harsh ambient conditions, minimizing the cost of energy for heating and cooling that would normally be incurred to accommodate ambient temperature swings caused by weather if the biomass is always stored in an outdoor PBR array. During cold winter nights, the biomass can be brought indoors to conserve thermal energy. High energy efficiency can be achieved when the heat sink consists of a second holding tank and a second tubing array, and the swings in the ambient temperature are exploited to add or reject energy from the biomass cultivation.

23 Claims, 6 Drawing Sheets

Related U.S. Application Data

(60) Provisional application No. 61/639,921, filed on Apr. 28, 2012.

(51) Int. Cl.
  *C12M 1/34*   (2006.01)
  *C12M 1/36*   (2006.01)
  *C12M 1/12*   (2006.01)
  *C12M 1/02*   (2006.01)
  *C12Q 3/00*   (2006.01)

(52) U.S. Cl.
  CPC ............ *C12M 41/18* (2013.01); *C12M 41/48* (2013.01); *C12Q 3/00* (2013.01)

(56) References Cited

U.S. PATENT DOCUMENTS

| | | | |
|---|---|---|---|
| 2008/0311649 A1* | 12/2008 | Cloud | C12M 21/02 435/292.1 |
| 2010/0028976 A1* | 2/2010 | Hu | C12M 21/02 435/257.1 |
| 2011/0180395 A1* | 7/2011 | Tucker | C02F 1/008 204/228.6 |
| 2011/0201063 A1* | 8/2011 | Mitropoulos | C12M 21/02 435/134 |
| 2013/0288228 A1* | 10/2013 | Anderson | C12M 23/06 435/3 |
| 2014/0004600 A1* | 1/2014 | Tarassov | C12M 21/02 435/292.1 |
| 2015/0196002 A1* | 7/2015 | Friesth | A01G 1/001 47/62 R |

* cited by examiner

METHODS AND APPARATUSES FOR CULTIVATING PHOTOTROPIC MICROORGANISMS

CROSS-REFERENCE TO RELATED APPLICATIONS

This application claims priority as a continuation in part of U.S. Ser. No. 13/872,084, filed 27 Apr. 2013, and thence to its priority application U.S. application 61/639,921, filed 28 Apr. 2012, each of which is incorporated herein by reference.

BACKGROUND

The United States and the rest of the world are facing significant challenges in finding sustainable replacements for petroleum products, which are extensively used for agriculture and transportation. Cultivated or farmed phototropic organisms, such as algae, are excellent candidates for meeting both needs, as well providing a feedstock for a variety of other products, including nutraceuticals and plastics, to name but a few. It should be understood that while the concepts disclosed herein can be applied to many different types of phototropic organisms, such concepts are particularly well suited to the cultivation of algae, both naturally occurring and engineered strains. Development of a cost-effective algae cultivation system is a key to facilitating wide-scale adoption of algae biomass farming.

The worldwide demand for algae biomass is growing. In the near future the market for nutraceuticals derived from algae (as forecast by the Nutrition Business Journal) is expected to be $500 billion in the U.S. alone, and over $2 trillion worldwide, with room for substantial growth. Pike Research predicts that the biofuel market will grow to $247 billion by 2020, up from $76 billion in 2010. The Biofuels Digest projects that algal biofuel capacity will reach 1 billion gallons by 2014. Algae wholesalers are targeting an annual production of 1.62 billion gallons, at a wholesale cost of $1.30 per gallon in 2014.

Global demand for alternative fuels is expanding, due to population growth, increased attention to energy security, and environmental policy mandates. For example, the Environmental Protection Agency established a renewable fuel volume requirement of 1.35 billion gallons in 2011. The U.S. Navy has publically announced its goal of fueling at least 50 percent of its fleet using renewable fuel sources by 2020. Achieving that objective will require a significant use of biofuels. There is also a growing demand for bio sourced oils to supplant the market currently met using soy oil and rapeseed oil.

A study by the University of Minnesota indicates that algae derived biomass performs as well as alfalfa in dairy cattle diets. If cultivation techniques can be provided on a cost effective basis, cultivated algae can provide a valuable oil fraction, a high-value protein co-product, and algae derived meal for animal feed; all while absorbing carbon dioxide from greenhouse gas emissions.

The following algae facts provide insight as to the potential of algae cultivation:

Algae's growth is phenomenal: to translate it agriculturally, algae crops grow 20 to 30 times faster than any other food crop.

Output is staggering: algae can produce 6,000 gallons of oil and 98 tons of meal per acre—every year. That's about 30 to 100 times more than other alternative biofuel sources, such as soybeans.

Algae biomass provides the most rapidly harvestable biofuel feedstock: Algae colonies can reach harvest size in as little as 48 hours, and appropriately designed cultivators can harvest algae biomass continuously.

Algae biomass absorbs large amounts of carbon dioxide ($CO_2$) while growing. Approximately 180 tons of $CO_2$ are absorbed annually from the atmosphere per acre of algae, and algae absorbs other greenhouse gases as well.

Appropriately designed cultivators make very efficient use of water; 85-97% of all water can be recovered and reused.

Algae biomass derived oil is suitable for use in existing petrochemical refineries and distribution systems. Ethanol, in comparison, is an aggressive solvent; requiring modifications to existing infrastructure, resulting in additional cost.

Algae biomass derived meal is high in protein (39%) and is suitable for use as animal feed and as nutritional supplements. Algae are even used directly as a food source by consumers in some cultures.

Algae-based fuels are considered to be carbon neutral. When burned, they offer a 50 to 80 percent reduction in particulate emissions versus fossil fuels, with no loss of power. Carbon emissions from algae derived fuel is offset by the $CO_2$ absorbed from the atmosphere during the cultivation of algae.

Algae-based fuel is naturally sulfur-free (sulfur needs to be removed from some types of petroleum crude oil, increasing the cost of refining).

Just 15,000 square miles of algae farms could replace all the petroleum used in the U.S. per year, according to the Department of Energy. That is about one-sixth the size of Minnesota.

There is a need for methods and apparatuses to efficiently cultivate phototropic organisms such as algae. There is a need for an algae growing system that a farmer can purchase, and within one or two months be growing algae, monitoring his crop for nutrients and harvesting using computerized controls. Such a system should have a return on investment (ROI) measured in a number of years, and that ROI should be competitive with the ROI on conventional farm equipment, such as tractors, cultivators, and other agricultural tools having a life cycle suitable for financing.

Some biofuel companies have emphasized algae growing systems that have high production rates, yet are capital and labor intensive. Others have emphasized open-pond systems that have low capital investment requirements, but are susceptible to environmental contamination and harsh weather extremes in most locations. There is a need for algae cultivating systems that operate with good yield, high reliability and low maintenance, but require a modest capital investment, thus providing a predictable financial return. There is also a need for energy efficient and economical growing systems that do not require large amounts of electrical or chemical energy for heating the biomass cultivations in the spring and fall seasons in temperate zones to keep them at optimal growing temperature during the early morning and late afternoon hours. Similarly there is a need for energy efficient and economical growing systems that do not require heat- or electricity-driven refrigeration systems in the summer to cool the biomass cultivation. Using electricity or natural gas for daily heating and/or cooling of the biomass cultivation may render the growing operation non-viable from an economic standpoint.

There is a need for all-weather, temperate-climate algae cultivating systems that are easily deployable, easy-to-use, easy-to-clean, and cost effective. In temperate climates, summer daytime temperatures can be too hot for growing certain algae, but summer nights generally cool off substantially. In the spring and fall, day time temperatures are good for growing, mornings are often quite cold, and often at or near freezing conditions. Because of these seasonal variabilities in high and low temperature extremes, and because of large diurnal temperature swings, there is a need for algae growing systems that are energy-efficient, such that they do not require large externally-supplied energy loads for heating and cooling the growth media to keep it at or near its optimal growing temperature.

SUMMARY

The inventions disclosed herein provide versatile energy-efficient closed loop phototropic organism growing systems for temperate climate zones, and methods for efficiently cultivating phototropic organisms, including but not limited to algae. Such systems and methods share the characteristics of being relatively energy efficient, and having relatively high production rates. Such systems are suitable for operating in urban or remote environments. Such systems can be operated in most temperate-zone environments year round to cultivate algae for a multitude of applications although at northern latitudes, growing may not be possible in winter.

In at least one embodiment, the cultivation systems disclosed herein are of a modular design (such that major components can be shipped directly to the site), can be quickly assembled in the field, and are automated with robust off-the-shelf industrial control systems equipped with a simple user interface. Growers/cultivators can use such systems to cultivate biomass to be used as animal feed, nutraceuticals, pharmaceuticals, green chemicals and biofuels. Significantly, waste water or brackish water can be used as a growth medium, further enhancing the economics and societal benefits of the systems.

Algae growing systems are generally categorized into 'open pond' systems and 'closed loop' systems. The biomass cultivation systems disclosed herein are based on closed loops, which are not exposed to unfiltered ambient air, and therefore are not contaminated by windblown particles. The closed loop systems disclosed herein employ photo-bioreactors (PBR), in which algae colonies are exposed to sunlight through transparent plastic tubing disposed in the ambient environment. One aspect of the concepts disclosed herein is the combination of an externally disposed PBR array (i.e., one or more individual PBRs) with an internally disposed holding volume, where the holding volume is protected from the temperature swings of the ambient environment to which the externally disposed PBR array is exposed. The internally disposed holding volume, temperature sensors, a pumping system and computerized control systems enable algae to be transferred from the internally disposed holding volume to the externally disposed PBR array (and vice-versa), enabling temperature control of the algae growth medium (water) to be achieved at a relatively lower total energy cost as compared to closed loop systems that primarily use chillers and/or heaters to moderate the temperatures in externally disposed PBRs, due to the heat sink effect of the internally disposed holding volume and due to the insulation provided by the indoor environment protecting the algae growth medium from the extremes of the ambient environment.

Most of the word's cultivated algae crops are grown in tropical or sub-tropical climates where temperatures are warm year-round and freezing temperature are very rare or absent. However, Masojidek et al. (J. Appl. Phycol. 2009, Vol. 21, p. 55-63) describes a phototropic growing system suitable for temperate climates that is based on PBR arrays. Masojidek's system incorporates the ability to drain to an indoor holding tank when the algae is exposed to non-optimal (high) temperatures, and to control the temperature of the algae in the holding tank by virtue of a heat exchanger coupled to a supply of hot, warm and cold service water. Desired temperatures are maintained with a control system capable of sensing temperatures and opening and closing electromagnetic valves. Masojidek et al. do not discuss a means for providing hot, cold and warm water for large scale growing systems where the energy demand to produce this service water is likely to be very costly, rendering the system non-viable from an economic standpoint.

In an exemplary embodiment of the present invention, a biomass cultivation system combines energy management using the ambient environment combined with outdoor growing in a PBR array. If it gets too cold or too hot outside, the system will automatically move the algae out of the external PBR tubing to an indoor holding tank. A second indoor tank serves as an energy storage reservoir. For example, on hot summer days the system will cool the thermal storage water by pumping the water through a second outdoor array during the night when temperature are cool, thereby using the diurnal temperature variance to reject heat energy from the thermal reservoir. The next day, this cool water can be used to cool the algae growing media by pumping the cool water through a heat exchanger disposed inside the algae holding tank. This "dual array-dual tank" configuration allows excess thermal energy in the algae growth media to be rejected to the ambient environment with minimal energy expense. As a second example, on a cool spring or fall day, the algae will be colder than optimal when circulated in the PBR array in the morning. However, the thermal storage water tank can be warmed up by circulating the water though the second outdoor array in the heat of the day. This reservoir of warm water can then be used that evening to heat the algae growth media by circulating the warm water through the heat exchanger disposed inside the algae growth media holding tank. Thus, energy from the ambient environment during the heat of the day provides the thermal energy necessary to maintain the algae growth media at or near the optimum growing temperature.

Example embodiments of the present invention also can provide a method of facilitating algae production, in which a vendor provides components to algae farmers, as well as providing monitoring services to such farmers on a periodic basis. Such monitoring can include water analysis for establishing optimal algae growing conditions, and algae strain analysis. Another method disclosed herein involves a business entity that both manufactures algae growing systems, and operates algae farms for profit, using equipment of their own design and manufacture.

In at least one exemplary embodiment, a biomass cultivation system includes PBR arrays fabricated out of relatively large diameter plastic tubing that can be rigid or flexible and a variety of cross-sectional shapes. In at least one such embodiment, 40-foot long sections of round 12" diameter rigid plastic tubing are employed. Longer sections of larger tubing can be more economical on a unit of capacity basis, because there are fewer tubing joints and fewer total components, which can increase system reliability and availability, and can reduce installation time. Non-rigid plastic tubes or rigid tubes of non-circular cross sections can have advantages with respect to cost of fabrication or cost of maintenance or light exposure.

In at least one exemplary embodiment, a biomass cultivation system includes racking elements configured to allow full gravity drainage of the PBR with a minimum volume of growth medium left in the tubing. Rigid plastic tubing can have a tendency to warp and sag in the heat of summer if not properly supported. The volume of material remaining in the tubing after it has been drained is referred to as "hold up." Similarly, tubing laid out flat will not drain quickly or completely. To minimize hold-up, the PBR array should not have periodic dips in the tubing caused by uneven settling of the ground, or sags between support elements. Such dips and sags can result in sections that tilt upward in the direction of flow. In an exemplary embodiment, the racking elements provide sufficient support to prevent sagging over time, and also to maintain the concentricity of the tubing. The support structure for the tubing used in the PBR is configured such that an inlet end of the PBR can be elevated with respect to an outlet end of the PBR, so that when the outlet is opened, the growth medium in the PBR flows or drains through the outlet due to gravity. In some applications a slope of at least 4 inches per 40 feet of tubing length can be suitable.

In at least one exemplary embodiment, a biomass cultivation system includes sensors and control inputs facilitating the measurement and control of at least one of the following: optical density, $CO_2$, pH, salinity, fixed nitrogen, phosphate and/or other nutrient levels in the PBR array. More advanced instrumentation can also be suitable, for example mass or infrared absorption spectrometers to monitor concentrations of lipids, proteins and carbohydrates or other compounds such as carotenoids or for microbial contaminants such as fungi. Other sensors and control systems can enable temperature and light exposure to be similarly measured and controlled. Too much light can be harmful, and if ambient conditions indicate too much light is present, the biomass can be moved indoors into the holding volume.

In at least one exemplary embodiment, a biomass cultivation system includes an auxiliary temperature control system (heating, cooling, or both) for the algae growth medium to augment the ambient temperature control provided by the holding volume. A suitable auxiliary heating and/or cooling system can be configured using a variety of commercially-available components. In an exemplary embodiment, a heat pump is used for additional thermal conditioning. In such an embodiment, either the ambient air or buried tubing can be used as the thermal reservoir.

In at least one exemplary embodiment, a biomass cultivation system includes sensors and control inputs facilitating the measurement of algae density. This is typically reported as a biomass dry weight in grams per liter of solution. The inventions disclosed herein further encompass systems including sensors for biomass quality parameters, such as lipid content or protein content. A control system can use such measurements to maximize the biomass value, and automatically trigger harvesting when conditions meet predetermined parameters. In at least one exemplary embodiment, harvesting can be implemented from the holding tank when the growing phase has been completed.

In at least one exemplary embodiment, a biomass cultivation system includes one or more processing volumes or holding volumes that are configured to enable algae and algae growth medium to be moved through the system using gravity feed as well as pumping. In an exemplary, but not limiting embodiment, the high point in the fluid system is where the growing solution enters the PBR array. Throughout the PBR array, the flow path is slightly downward all the way to the exit of the PBR. From there, the flow is pumped into the holding tank (e.g., the top or bottom of the tank), or alternatively, up slightly to the PBR array entry point. This flexibility allows biomass value to be maximized based on the type of algae being grown, the stage of the growth in the algae lifecycle, nutrient conditions, sunlight conditions and ambient temperature. The downward flow path also helps minimize holdup, which is generally undesirable. The holdup has algae in it, and as the holdup dries it becomes sludge and can be difficult to remove without taking the system apart. Minimizing holdup can help to maintain high system availability, minimize maintenance cost and maximize algae production.

In at least one exemplary embodiment, a biomass cultivation system includes a sanitizing system that generates a chlorine based disinfectant solution from brine and electricity. A commercial supplier of such systems is Miox, Inc. of Albuquerque, N. Mex. A control system can automatically sanitize the PBR array (and if desired, the holding volume) after one or more harvest cycles are complete.

In at least one exemplary embodiment, a biomass cultivation system is provided with major system components integrated into a portable, easy to transport skid mounted system. PBR arrays can be fabricated on the end user's site using plastic tubing, as an example. Components that can be provided on one or more such skids include one or more controllers, small tubing (not associated with the PBR array), racking for the array, fittings, pump(s), valves, an optional auxiliary lighting system, sanitizing system and an auxiliary heating and cooling system. In some embodiments a back-up generator or solar array for power can also be provided. In at least some embodiments, the large diameter tubing for the PBR array can arrive in a 40 foot shipping container hauled by rail and/or tractor trailer. The holding tanks can also arrive by tractor trailer. A tilt-up building on a reinforced slab can be employed for the structure.

This Summary has been provided to introduce some concepts related to the present invention in a simplified form that are further described in detail below in the Description. However, this Summary is not intended to identify key or essential features of the claimed subject matter, nor is it intended to be used to determine the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates the basic functional elements employed in an exemplary embodiment of an algae cultivating system in accord with the present inventions;

FIG. 2 schematically illustrates a building protecting the holding volume from an ambient environment while the PBR element is disposed outside, in the ambient environment, to expose the algae to sunlight;

DESCRIPTION

Figure 1:
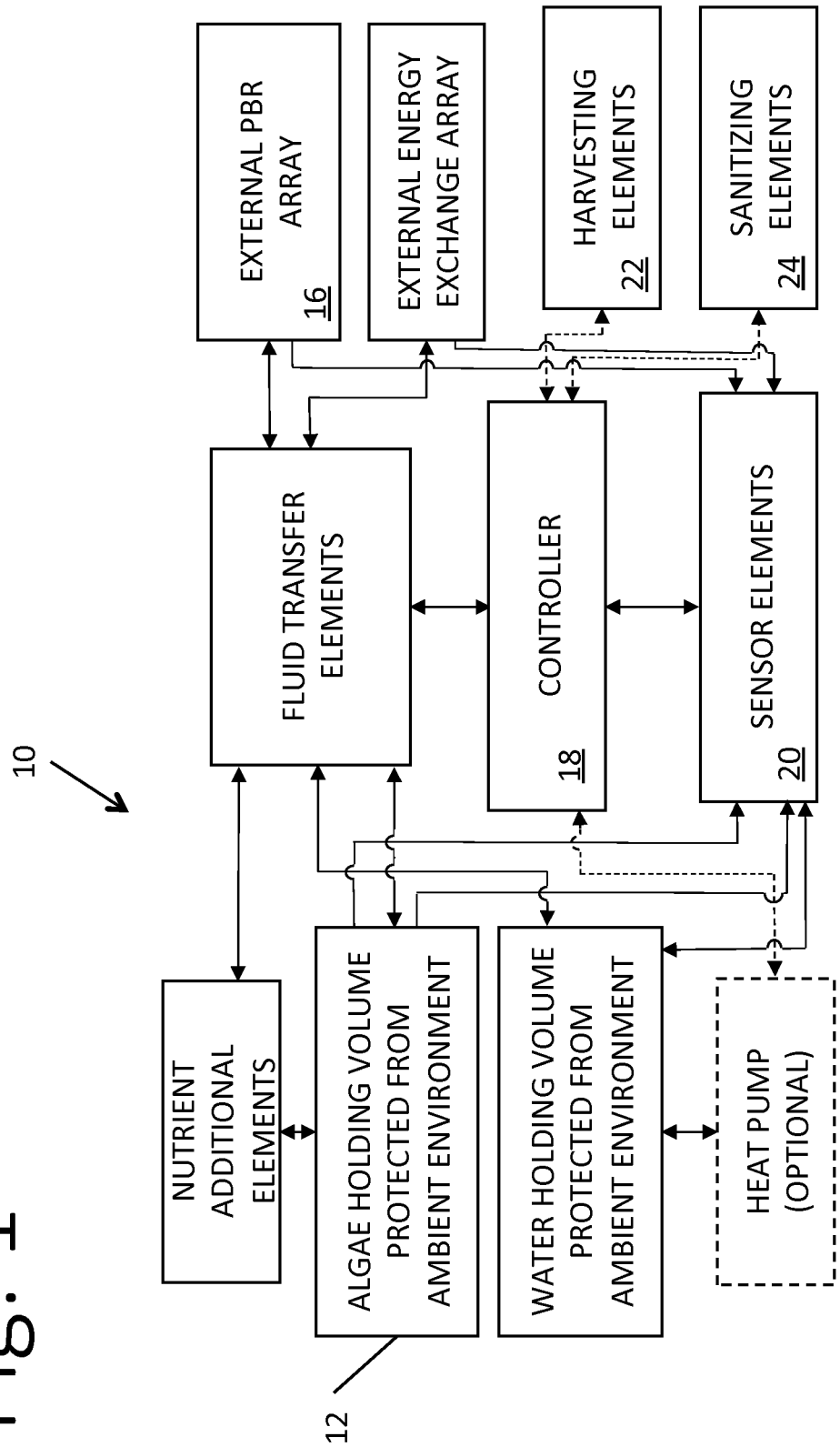

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

Disclosed herein are methods and apparatuses for biomass cultivation (using algae in an exemplary embodiment) incorporating photo bio-reactor (PBR) technology coupled with a heat sink to increase energy efficiency. A PBR array can be coupled to an indoor storage tank system (the heat sink). The indoor storage tank system can have a volume equal to or greater than the volume of the PBR array, which is located outside. A controller can be used to optimize the growth of biomass by optimizing three key growth parameters: exposure to sunlight, exposure to the optimal temperature, and exposure to nutrients. The indoor tank system serves as a holding volume to be used when ambient conditions in the PBR array are inimical to growth, minimizing the cost of energy for heating and cooling that would normally be incurred to accommodate ambient temperature swings caused by weather or are otherwise inherent to the climate zone, if the biomass were always stored in an outdoor PBR array. When the sun is intense or the outdoor temperatures are extremely hot or cold, exposure to these elements can be minimized, optimizing growth for those conditions. During cold winter nights, the biomass can be brought indoors to conserve thermal energy. During hot summer extremes, biomass can be circulated through the PBR at night to release stored thermal energy back to the environment.

Other aspects of the concepts disclosed herein can include adding a second holding tank, which serves as a thermal energy reservoir, and a second outdoor array used to gain or reject heat from the thermal energy reservoir. This second outdoor array can be used to gain or reject heat from the ambient environment as desired. Chlorinated water can be used as the thermal energy storage fluid, but it could also be some type of oil. An additive, such as a dye, can be added to the thermal energy fluid to enhance its adsorption of solar energy in the spring and fall when cool temperatures prevail. A dye might also be added in summer to increase the fluid's emissivity (for example, when it is desired to reject heat back to the environment at night after a hot summer day). Alternatively, the second outdoor array can be painted black to enhance heat transfer to and from the array to the ambient environment. To reject heat, the water can be circulated through the reservoir at night when the ambient temperature is below the water temperature in the thermal reservoir. To gain heat from the ambient, which can be used to heat the algae growth media during cool mornings in the spring and fall, the water can be circulated in the array during the peak afternoon temperatures. A heat pump can be added to the system to augment the heating the cooling provided by the ambient environment on account of the diurnal temperature swings described above. Automated control of these elements can be achieved by including temperature sensors and electronically-controlled valves in communication with a system controller.

Other aspects of the concepts disclosed herein include coupling the indoor storage system to a gravity drain system, an integrated disinfection system incorporating on-site generation of disinfectant from brine, and large diameter PBR technology incorporating technology to reduce biofilm growth on the PBR tubing surfaces. An automated system for adding nutrients the algae growth medium while it is in the holding tank can be incorporated using nutrient sensors and a control system.

FIG. 1 schematically illustrates some basic functional elements employed in an exemplary algae cultivating system in accord with the concepts disclosed herein. It should be understood that while the following discussion emphasizes the cultivation of algae, the concepts disclosed herein can be employed to cultivate other phototropic organisms.

Referring to FIG. 1, an exemplary system 10 includes a holding volume 12, one or more fluid transfer elements 14, an external PBR array 16 (recognizing that the concepts disclosed herein encompass a single external PBR, as well as an plurality of individual PBRs), a controller 18, and one or more sensor elements 20. Optional additional components can include harvesting elements 22 and sanitizing elements 24.

Holding volume 12 provides a quantity of growth medium (generally fresh or brackish water, and/or waste water) that is protected from ambient temperatures. If necessary, heating or chilling elements can be employed to thermally condition the liquid inside the holding volume. However, in many locations, merely providing a holding volume that is protected from the ambient volume will enable the growth medium to be moved out of the external PBR into a protected area where the algae colony in the growth medium is protected from harmful temperature swings.

In an exemplary embodiment, a secondary tank is employed to store a quantity of water to function as a thermal mass, to enable thermal management of growth medium moved into the holding volume. In such an embodiment, the water in the secondary tank is used as a coolant to exchange heat with the contents of the holding volume, for example by exchanging heat within a heat exchanger located inside the holding volume. This provides additional thermal management capabilities with a relatively modest capital and energy cost. In addition to the secondary tank and the heat exchanger in the holding volume, a pumping capability can be provided. Note most embodiments include a pump, and with proper valve arrangements an existing pump can be used to drive the water from the secondary tank through the heat exchanger in the primary tank (the holding volume). The heat exchanger includes a first portion disposed in the primary tank, and a second portion disposed proximate the ceiling of the building or near the ground. The heat exchanger can be implemented by a small tube array (to promote heat transfer). This tubing does not need to be clear (and in some applications can work best if it is black), but minimizing hold-up can be good to avoid freezing in the tubes in the winter.

In at least some embodiments, the secondary tank (functioning as a heat exchanger) has a capacity that has been selected to be sufficient to provide a desired amount of thermal conditioning to the growth medium during a 24 hour growing cycle. That volume can be selected, for example, based on winter or summer extreme temperatures. With respect to winter extremes, the volume of the secondary tank can be selected to provide enough relatively warm water to prevent the growth medium stored in the holding volume from cooling to a point that a viability of the algae colony is reduced. With respect to summer extremes, the volume of the secondary tank can be selected to provide enough relatively cool water to prevent the growth medium stored in the holding volume from warming to a point that a viability of the algae colony is reduced. Note that whenever a temperature of the growth medium in the PBR array reaches above or falls below a predetermined value, some or all of the growth medium can be moved into the holding volume so that the heat exchanger described above can thermally moderate the temperature of the growth medium. In extremely warm sunny climates, the growth medium might need to be moved out of the PBR once or more per day, to prevent the growth medium from getting too hot. Similarly, in extremely cold climates, the growth medium might need to be moved out of the PBR once or more per day, to prevent the growth medium from getting too cold.

In at least some embodiments, the holding volume has a capacity that is sufficiently large such that all of the growth media from the PBR can be transferred into the holding volume. Such embodiments can be of particular use when the night time temperatures fall so low or day time temperatures that are so high as to create hostile conditions for the algae.

In another exemplary embodiment, the holding volume has a capacity greater than the volume of the PBR array. In such an embodiment, the total volume of colonized growth medium can exceed the volume of the array. When the array is full with colonized growth medium, the growth medium can be circulated through the array and mixed with the growth medium remaining in the holding volume as it exits the array. The colonized growth medium in the holding volume can remain well mixed. The feed from the array can also come from this tank, and nutrients and CO2 can be added as needed in using automated controls. With this configuration, assuming ample days of sunlight, biomass production per unit volume of array can be greater than that achievable if the array and holding volume are of equal volume. This embodiment can be preferred in many locations across the planet where productivity is not limited by sufficient sunlight.

In an exemplary embodiment, the holding volume does not dilute the growth medium in the PBR array, as the holding volume does include a mass of water (unless the growth medium from the PBR array is moved into the holding volume). In such an embodiment, when the PBR array is full, the holding volume is empty. There is no "secondary water" in the holding tank to dilute the algae growth medium. The holding volume is like a barn, and the algae are like cows. Some or all of the algae/cows are outside in the PBR, or inside in the barn depending on whether the conditions outside are beneficial.

It should be understood that holding volume 12 can be implemented as a single structure or a plurality of different structures. In at least one embodiment the holding volume is a single tank. In an exemplary embodiment, the holding volume tank is a polymer tank. In an exemplary system, the PBR array is about 50,000 gallons, and three 17,000 gallon holding tanks are employed inside a protected area to implement the holding volume. It should be recognized that the concepts disclosed herein encompass embodiments wherein the holding volume itself is a PBR. Such a PBR will be inside a building, protected from harsh ambient temperatures. Windows, skylights, or light pipes can be used to direct sunlight into the internal PBR for additional algae growth. Artificial lighting can also be used, although such lighting will consume electricity, and depending on local instantaneous electricity cost, the additional algae growth may not offset such cost (or justify the additional capital expense of the second array with lighting).

Fluid transfer elements 14 are included to enable water (i.e., growth medium) to be transferred between the holding volume and the external PBR. Fluid transfer elements can include pipes, valves, and one or more pumps. In an exemplary embodiment any actuatable elements (such as valves and pumps) are controllably coupled to controller 18, so that such elements can be actuated automatically. In an example embodiment, at least one gravity assisted fluid transfer element can be included. For example, the holding volume can be elevated, such that when appropriate valving is opened, the growth media in the holding tank naturally flows into the external PBR.

PBR 16 is disposed outside, where the algae in the PBR can be exposed to sun light to stimulate algae growth. Some PBRs are fabricated from small diameter tubing. While efficient at light capture, such tubing is more expensive to install and maintain. In an exemplary embodiment, the PBR is fabricated from 12 inch diameter clear polymer tubing, which is much easier to install and clean. Relative to 12 inch tubing, an equivalent array volume using 6 inch tubing would require four times as much tubing length, resulting in four times as many sections of 40 foot tubing to install and clean, four times as many joints to maintain, etc.

In at least some embodiments, a robust coating can be applied to the inside of the tubing to reduce or inhibit algae from attaching to the tube wall and to inhibit or reduce bacterial biofilm growth. Oligocide, Inc., of Albuquerque, N. Mex. is an example of a vendor for coatings and additives that inhibit biofilm growth in polymeric materials. Paralene, silica or PTFE coatings can reduce algae wall attachment.

Controller 18 is used to monitor the system, and perform specific functions based on system inputs. Controller 18 can be implemented using custom logic circuits or a general purpose computing device executing machine instructions to implement specific functions. In an exemplary system, controller 18 is implemented using one or more programmable logic controllers (PLCs). A PLC is a digital computer used for automation of electromechanical processes, such as control of machinery on factory assembly lines, amusement rides, or light fixtures. PLCs are used in many industries and machines. Unlike many general-purpose computers, the PLC is designed for multiple inputs and output arrangements, extended temperature ranges, immunity to electrical noise, and resistance to vibration and impact. Programs to control machine operation are typically stored in battery-backed-up or non-volatile memory.

Sensor elements 20 can include at least one or more temperature sensors for determining the temperature inside the PBR. In some embodiments, temperature sensors are also used to determine a temperature inside the holding volume, allowing more accurate determination of how much growth medium needs to be transferred between the holding volume and the PBR to achieve the desired thermal conditioning, in embodiments where both the PBR and holding volume are partially filled with growth medium.

Additional optional sensor elements include one or more flow rate sensors, to measure a flow of water between the holding volume and the PBR.

In at least one embodiment, the system includes a sensor or combination of sensors configured to evaluate the growth medium in the PBR to determine if additional nutrients are required. That information can be conveyed to the controller, to trigger the activation of a nutrient supply system (not shown). Exemplary sensors include, but are not limited to, a $CO_2$ sensor, a fixed nitrogen sensor, and a phosphate sensor.

In at least one embodiment, the system includes a sensor configured to evaluate whether the algae colony is ready to harvest. Exemplary sensors include, but are not limited to, UV, visible or infrared spectrometers, and/or a mass spectrometer. Turbidity meters, particle counters/sizers, and nephalometers can also be useful to estimate the bone dry biomass density. The density measurement is not only useful for the harvest decision, but can also be used to monitor growth rates throughout the growth lifecycle.

In at least one embodiment, the system includes optional harvesting elements 22, such that when the algae are ready for harvest, the controller can trigger the harvesting elements to harvest the algae crop. Harvesting elements include, but are not limited to pumps, filters, product tanks and centrifuges. The Pall Corporation of Port Washington, N.Y., is developing a filter system targeted to commercial growers of algae.

In at least one embodiment, the system includes optional sanitizing elements 24, such that after the algae are harvested, the controller can trigger the sanitizing elements to clean the PBR, readying the PBR for a new crop. MIOX Corporation of Albuquerque, N. Mex. is a developer of chlorine-based sanitizing systems that incorporate on-site generation of disinfectants. In an example embodiment, the sanitizing elements generate a chlorine based disinfectant from a brine solution. After harvest, the farmer can inoculate the growth medium in the PBR array or holding volume. The inoculant can be added with fresh water which has been suitably treated (for example, filtered and amended with nutrients and additives for pH control). In an exemplary embodiment, a separate small scale system (with triplicate redundancy) is provided to grow inoculant, so the farmer also has "seed corn" for his next planting. A small lab capability can also be provided to monitor the quality of the inoculant. The same sanitizing components can be used to sanitize the holding volume.

Not specifically shown are additional elements that can be beneficially included in system 10, including but not limited to nutrient delivery components (such as pipes, meters, and valves), nutrient supply volumes (holding one or more of carbon dioxide, nutrient rich waste water, nutrient concentrates, such as phosphorus and/or nitrogen), PBRs disposed inside a protective structure, ancillary light sources for algae growth at night or in PBRs disposed inside of the protective structure, and/or a pallet or skid upon which control equipment and/or pumps are integrated.

In an exemplary embodiment, filtered air is sparged into the holding tank when inoculating the growth medium. Sparging can also be provided during the growth cycle as required. In some embodiments, additional sparging can be implemented in the PBR array. In some embodiments, a supply of $CO_2$ is kept on hand and can be used to augment ambient filtered air for situations where higher concentrations of $CO_2$ are needed, and cost-justified. This can be highly specific to the strain and the instantaneous growing conditions.

It should be noted that in FIG. 1 harvesting elements 22 and sanitizing elements 24 are shown as being logically coupled to controller 18. It should be understood that both the harvesting elements and the sanitizing elements will be coupled in fluid communication with either or both of holding volume 12 and/or PBR array 16 as well.

Figure 2:
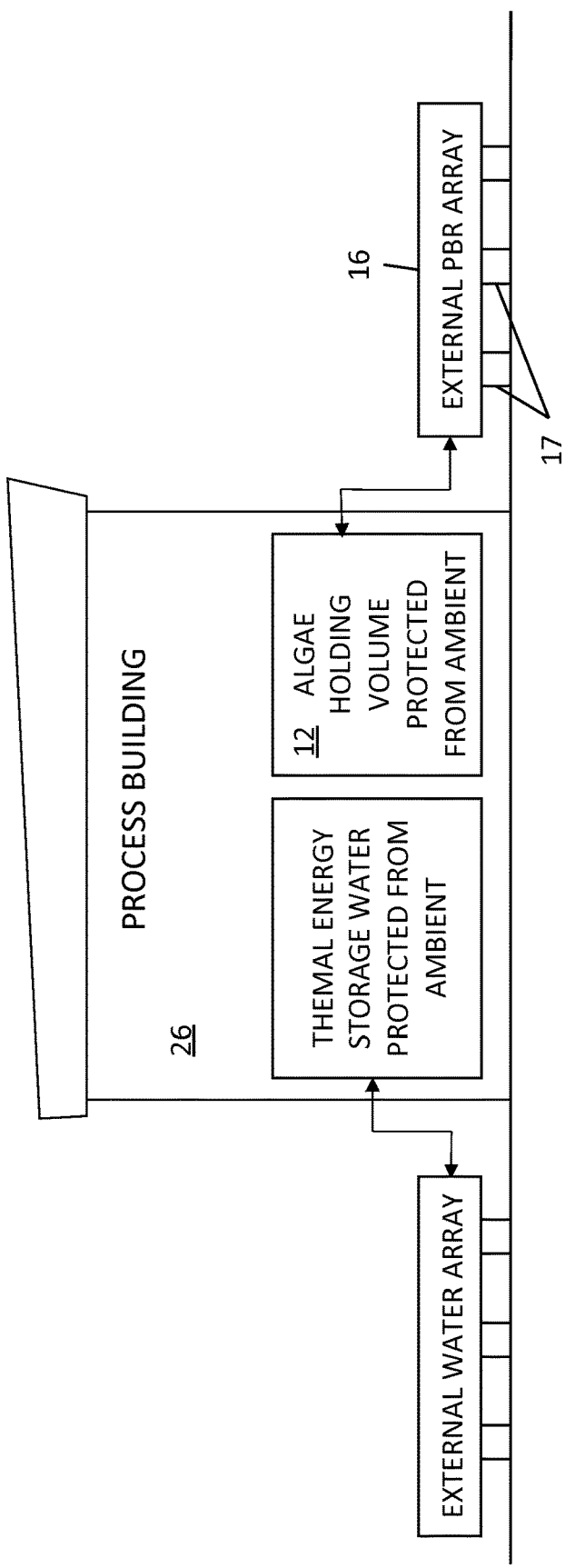

FIG. 2 schematically illustrates a building 26 protecting holding volume 12 from an ambient environment while PBR 16 is disposed outside, in the ambient environment, to expose the algae to sunlight. While not shown in FIG. 2, it should be understood that the concepts disclosed herein encompass embodiments wherein some portion of the PBR can extend into the building, which can enable a drain/outlet portion of the array to be in a weather protected area. A plurality of supports 17 can be used to keep PBR array 16 off of the ground. The number and spacing of supports 17 can be selected to prevent sagging in the array. Such sagging can undesirably lead to low spots where holdup can accumulate.

Figure 3:
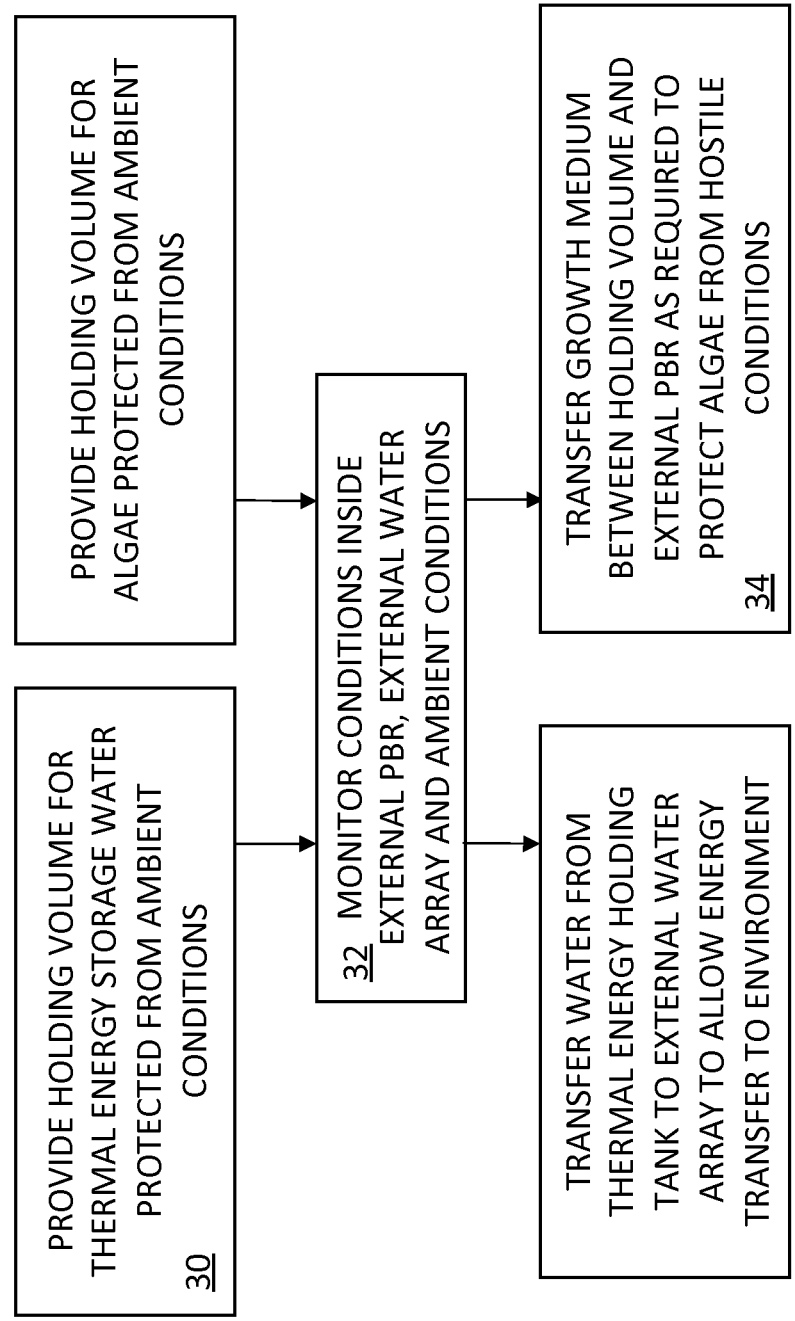
FIG. 3 is a flow chart of exemplary steps employed to cultivate algae in accord with the present inventions.

FIG. 3 is a flow chart of exemplary steps employed to cultivate algae in accord with the concepts disclosed herein. In a block 30 a holding volume is provided. As discussed above, the holding volume is protected from the ambient environment, and is of a sufficient size to enable some, if not all of the growth medium in the external PBR to be brought indoors. In a block 32, the conditions inside the external PBR are monitored. In a block 34, when temperature conditions in the external PBR raise above a predetermined level, or drop below a predetermined level, growth medium is moved between the PBR and the holding volume to moderate the temperature of the growth medium. In extreme conditions (such as a cold winter night), block 34 can result in the removal of all or most of the growth medium from the PBR. In some embodiments, block 34 can be implemented by circulating growth medium between the PBR and holding volume at a predetermined rate. In some embodiments, block 34 can be implemented by transferring a predetermined volume of growth medium between the PBR and holding volume as a discrete event (which can be repeated based on the monitoring function of block 32). In some embodiments, growth medium in the holding volume can be thermally conditioned to increase or decrease a temperature of the growth medium. Such thermal conditioning can be automated where temperature sensors and control mechanisms are provided. Since a system can be operated to willfully gain, store or release sensible heat energy, this capacity for energy management can be utilized to maintain the colony growth medium at conditions optimal for growing the value of the biomass. In an exemplary embodiment, *Haematoccocus pluvialis* algae creates astaxanthin, a valuable pharmaceutical, at a maximum yield within a temperature range of 22-25 C, but yield decreases very substantially outside that range. In another exemplary embodiment, a cyanobacteria *Spurulina* spp. grows optimally at 35 C. Colder temperatures are best to start the morning, but since the array acts as a solar concentrator, the algae growth medium is cooled to approximately 30 C at night. The temperature is allowed to rise to a maximum of 38 C during the heat of the day as an upper limit. Beyond this temperature the colony will overheat and the bacteria will die. In addition, *Spirulina* must be protected from too much light when the growth medium is below 25 C. In another exemplary embodiment, *Nannochloropsis* spp. are robust and while some variations in growing protocols are strain specific, optimum temperature for maximizing biomass growth of the biomass in the growing medium is normally 25-29 C. When a sufficient density of biomass has been produced during the growth stage, the temperature and/or nutrient protocols can be changed such that the colony can be starved of certain nutrients or optimal temperatures necessary for growth. This is known as stressing the colony, and the protocol is to switch from a "growth phase" to a "stress phase." This stress triggers the *Nannochloropsis* colony to convert starches and other intercellular compounds into lipids as a response to the stress. *Nannochloropsis* spp.

Evolved with this ability, but through natural strain selection or genetic engineering, a strain can be developed that will quickly convert greater than 50% of the total biomass into lipids. These lipids can be extracted from the biomass after harvesting the algae, and subsequently converted to biofuel or processed to extract nutritional supplements.

Certain of the method steps described above can be implemented automatically. It should therefore be understood that the concepts disclosed herein can also be implemented by a controller, and by an automated system for implementing the steps of the method discussed above. In such a system, the basic elements include the PBR, the holding volume, sensors to measure the temperature in the PBR, fluid transfer equipment to move growth medium into and out of the PBR and holding volume, and the controller. It should be recognized that these basic elements can be combined in many different configurations to achieve the concepts discussed above. Thus, the details provided herein are intended to be exemplary, and not limiting on the scope of the concepts disclosed herein.

Figure 4:
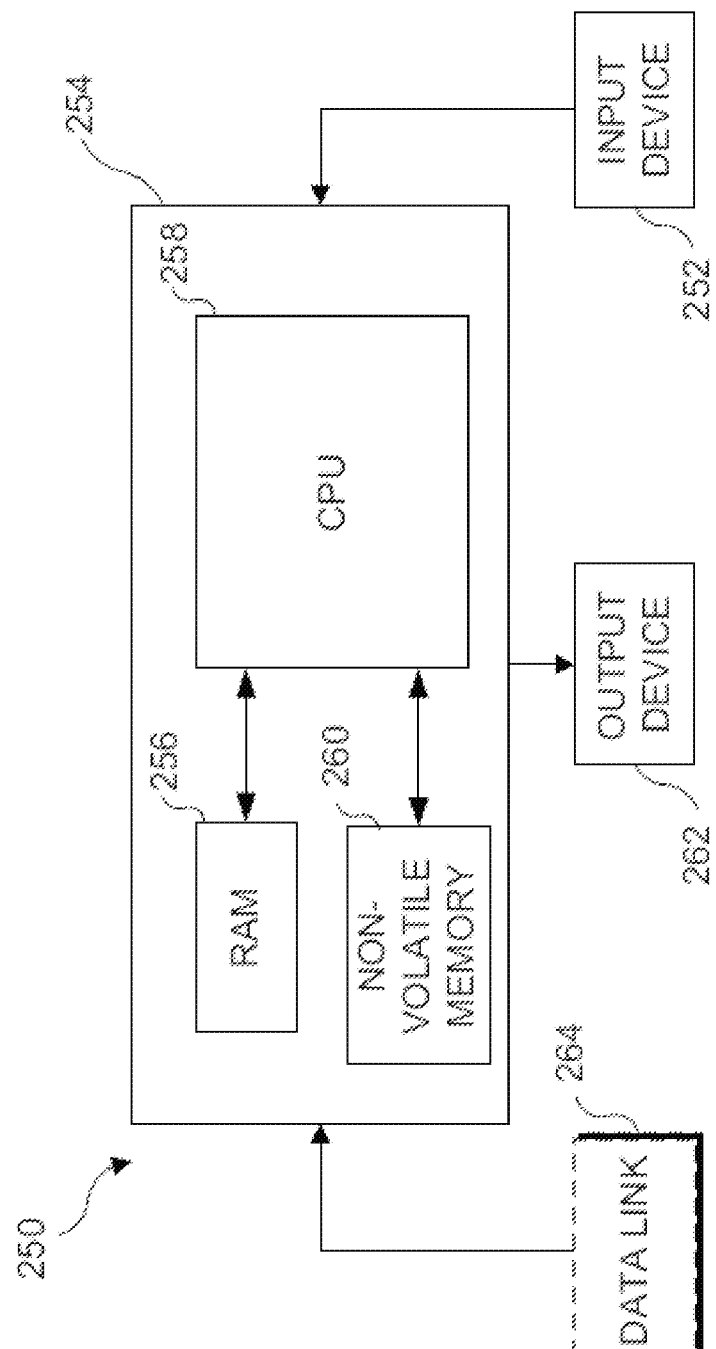
FIG. 4 is a functional block diagram of an exemplary computing device that can be employed to implement some of the method steps and control functions disclosed herein.

FIG. 4 is a functional block diagram of an exemplary computing device that can be employed to implement some of the method steps and control functions disclosed herein. It should be understood that while FIG. 4 describes a general purpose computing device executing specific software to implement the specific functions disclosed herein, the concepts disclosed herein also encompass the use of PLCs and/or application specific integrated circuits (ASIC) to perform the required processing functions.

FIG. 4 schematically illustrates an exemplary computing system 250 suitable for use in implementing steps 32 and 34 in the method of FIG. 3. It should be recognized that different ones of the method steps disclosed herein can be implemented by different processors (i.e., implementation of different ones of the method steps can be distributed among a plurality of different processors, different types of processors, and even processors disposed in different locations). Exemplary computing system 250 includes a processing unit 254 that is functionally coupled to an input device 252 and to an output device 262, e.g., a display (which can be used to output a result to a user, although such a result can also be stored for later review or analysis; noting that some embodiments, such as those using PLCs, do not always require displays). Processing unit 254 comprises, for example, a central processing unit (CPU) 258 that executes machine instructions for carrying out at least some of the various method steps disclosed herein. The machine instructions implement functions generally consistent with those described above. CPUs suitable for this purpose are available, for example, from Intel Corporation, AMD Corporation, Motorola Corporation, and other sources, as will be well known to those of ordinary skill in this art.

Also included in processing unit 254 are a random access memory (RAM) 256 and non-volatile memory 260, which can include read only memory (ROM) and may include some form of memory storage, such as a hard drive, optical disk (and drive), etc. These memory devices are bi-directionally coupled to CPU 258. Such storage devices are well known in the art. Machine instructions and data can be temporarily loaded into RAM 256 from non-volatile memory 260. Also stored in the non-volatile memory can be operating system software and other software. While not separately shown, it will be understood that a generally conventional power supply can be included to provide electrical power at voltage and current levels appropriate to energize computing system 250.

Input device 252 can be any device or mechanism that facilitates user input into the operating environment, including, but not limited to, one or more of a mouse or other pointing device, a keyboard, a microphone, a modem, or other input device. In general, the input device might be used to initially configure computing system 250, to achieve the desired processing. Configuration of computing system 250 to achieve the desired processing includes the steps of loading appropriate processing software into non-volatile memory 260, and launching the processing application (e.g., loading the processing software into RAM 256 for execution by the CPU) so that the processing application is ready for use. Output device 262 generally includes any device that produces output information, but will typically comprise a monitor or display designed for human visual perception of output. Use of a conventional computer keyboard for input device 252 and a computer monitor for output device 262 should be considered as exemplary, rather than as limiting on the scope of this system. Data link 264 is configured to enable sensor data collected by the algae growing system to be input into computing system 250. Those of ordinary skill in the art will readily recognize that many types of data links can be implemented, including, but not limited to, universal serial bus (USB) ports, parallel ports, serial ports, inputs configured to couple with portable memory storage devices, FireWire ports, infrared data ports, wireless data communication such as Wi-Fi and Bluetooth™, and network connections via Ethernet ports.

It should be understood that the term "computer" and the term "computing device" are intended to encompass networked computers, including servers and client device, coupled in private local or wide area networks, or communicating over the Internet or other such network. The data required to control the algae cultivating system can be stored by one element in such a network, retrieved for review by another element in the network, and analyzed by any of the same or yet another element in the network. Again, while implementation of the method noted above has been discussed in terms of execution of machine instructions by a processor (i.e., the computing device implementing machine instructions to carry out the specific functions noted above), at least some of the method steps disclosed herein can also be implemented using a custom circuit (such as an application specific integrated circuit or a PLC). In some embodiments control processing and sensor analysis is implemented locally (i.e., at the cultivation facility), but the concepts disclosed herein encompass sending data from the cultivation system to a remote computer for offsite processing and analysis.

Figure 5A:
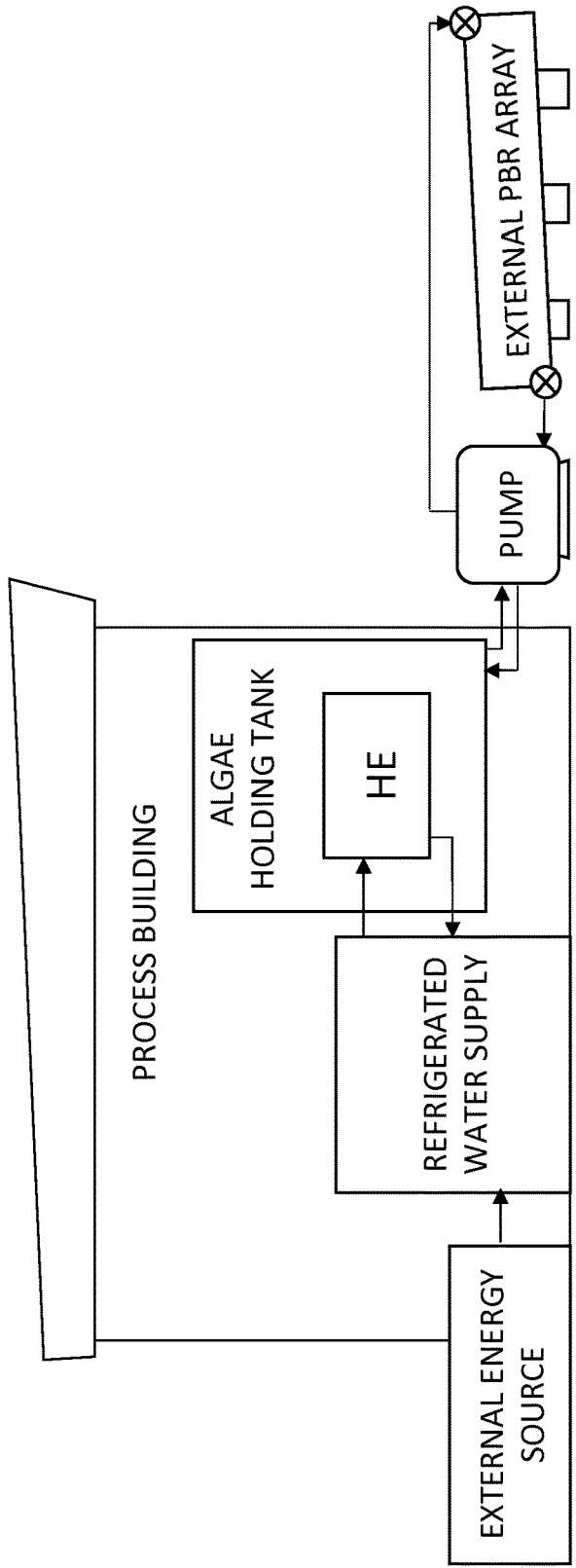
FIG. 5(A,B) schematically illustrate a prior art system, and an embodiment incorporating a gravity drain configuration for the PBR array with key elements for using diurnal temperature variations for thermal energy storage.
Figure 5B:
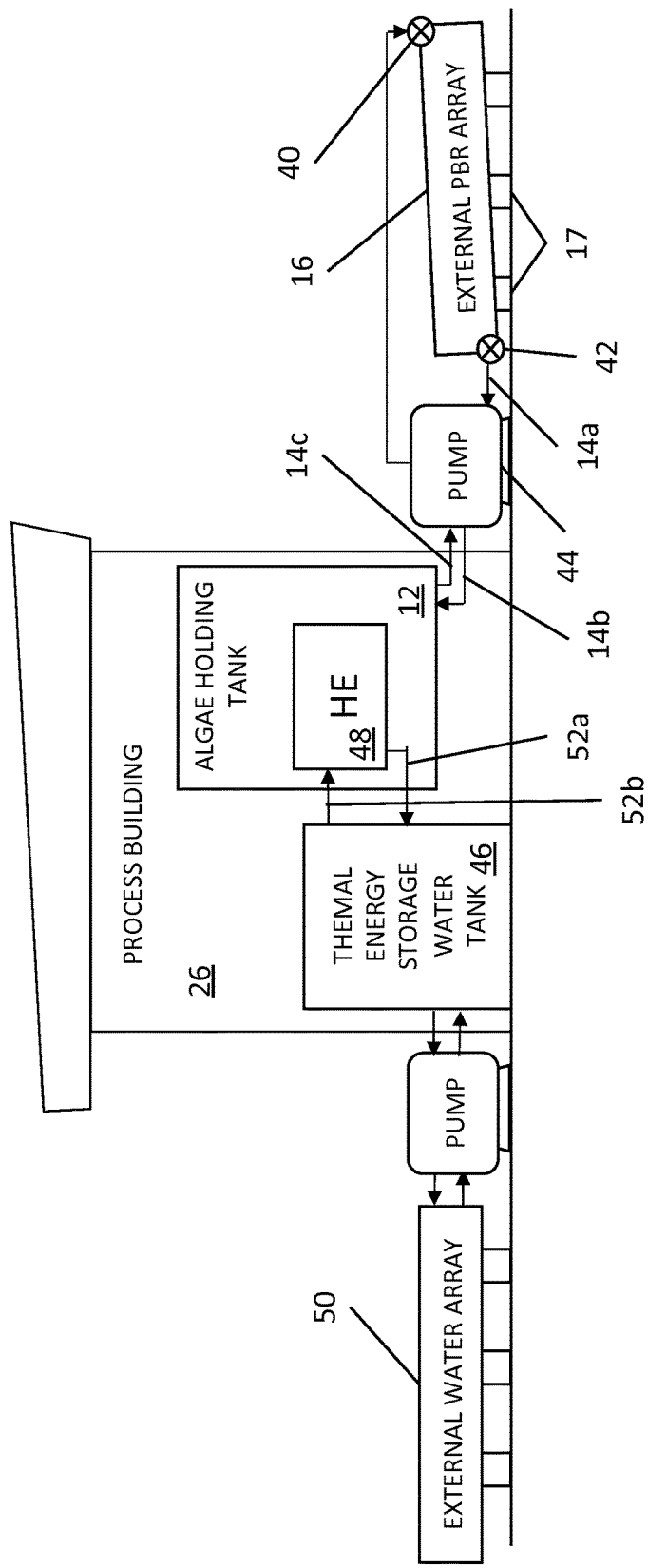

FIG. 5A is a PRIOR ART system of Masojidek et al. FIG. 5B is based on FIG. 2, and the same element numbers are employed for common elements. As shown in FIG. 5B, PBR array 16 includes an inlet 40 and an outlet 42. FIG. 5B schematically illustrates an exemplary embodiment incorporating an external water array 50 in fluid communication with a thermal storage tank 46 configured to exchange energy with the ambient environment in a manner that exploits the diurnal temperature cycles associated with temperate climate zones to minimize the amount of non-ambient heating and cooling required by the growing operation. Significantly, inlet 40 is higher than outlet 42, such that when PBR array 16 is emptied gravity will assist in evacuating the PBR. While not specifically shown, it should be understood that the fluid system schematically illustrated in FIG. 5B will include a plurality of flow control devices such as valves.

As noted above, holdup can increase maintenance costs, so the spacing and number of supports 17 can be selected to prevent sagging in the array. Such sagging can undesirably lead to low spots where holdup can accumulate. The number and spacing of the supports can also be sufficient to prevent the tubing from losing concentricity.

A pump 44 can be used to pump growth medium exiting outlet 42 into holding volume 12 inside building 26. The growth medium moves through a fluid line 14a into pump 44, and then through a fluid line 14b into holding volume 12.

When the ambient conditions in PBR array 16 are suitable for algae growth, growth medium from holding volume 12 will exit the holding volume via a fluid line 14c, and pump 44 can be used to direct the growth medium into inlet 40 of PBR array 16 via a fluid line 14d.

The algae cultivation system of FIG. 5B includes a thermal management system to provide additional thermal management abilities. A secondary tank 46 includes coolant (water in an exemplary embodiment). A pump (either pump 44 with appropriate fluid connections, or an additional pump, not specifically shown) is used to circulate coolant from secondary tank 46 into a first heat exchanger portion 48 disposed in primary tank 12 (via fluid lines 52a and 52b), or a second heat exchanger portion 50 near a roof of the building (via fluid lines 54a and 54b). In some embodiments, the second heat exchanger portion 50 can be near or in the ground, depending on ambient conditions. Thermal energy will be absorbed (or dissipated) by first heat exchanger portion 48, and thermal energy will be dissipated (or absorbed) by a second heat exchanger portion 50. The heat exchanger can increase overall system costs, but can provide a significant operational cost benefit in temperate climates.

It should be understood that the fluid system of FIG. 5B is exemplary, and that other fluid system configurations could be implemented to achieve a similar functionality. For example, the racking system can be configured such that as the algae leaves the primary tank, it flows downhill through the array. An airlift pump can be used to lift the algae back up to the top of the primary tank.

It should be further noted that rigid tubing made from other materials such as glass can be used, but has a higher initial cost. It can be less susceptible to sagging and can more easily break. Non-circular cross-sections can offer advantages for maintenance (e.g., a removable top cover) or for light penetration (a flattened oval cross-section allows more algal biomass exposure to the sun). Flexible tubing can also be used and replaced after each batch of algae is harvested. This is potentially cost-effective relative to glass or rigid plastic, but can generate more waste. If the flexible tubing is not under pressure, it will relax to the flattened oval cross-section mentioned above allowing for enhanced exposure.

The terms about and approximately, as used above and in the claims that follow, should be understood to encompass a specified parameter, plus or minus 10%.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

What is claimed is:

1. An apparatus for cultivating phototropic organisms in a growth media without the use of solar concentrators, the apparatus comprising:
   a photo-bioreactor (PBR) array comprising plastic tubing and disposed outdoors through which growth media comprising organisms is circulated using a first pump while the PBR array is exposed to sunlight;
   a holding tank for growth media comprising organisms disposed indoors and in fluid communication with the PBR array and the first pump and configured to receive the growth media comprising organisms from the PBR array;
   a first heat exchanger disposed inside the holding tank through which water is circulated using a second pump to regulate the temperature of the growth media comprising organisms;
   a water storage tank disposed indoors and in fluid communication with the first heat exchanger; and,
   a second heat exchanger array disposed outdoors through which water from the water storage tank is circulated using a third pump to regulate the temperature of water in the water storage tank by heat exchange with ambient outdoor air.

2. The apparatus of claim 1 wherein the PBR array comprises twelve-inch diameter plastic tubing.

3. The apparatus of claim 1 wherein the holding tank volume is greater than the volume of the PBR array.

4. The apparatus of claim 1 wherein the PBR array comprises an inlet and an outlet wherein the outlet is disposed lower than the inlet such that a fluid path through the PBR array between the inlet and the outlet follows a continuously descending path.

5. The system of claim 1 further comprising a plurality of PBR array supports wherein the number and spacing of the supports is sufficient to prevent sagging of the PBR array and to encourage tubing components of the PBR array to remain concentric.

6. The apparatus of claim 1 further comprising a control system configured to automatically implement at least one of:
   (a) moving the growth media comprising organisms from the PBR array to the holding tank to prevent the growth media in the PBR array from being exposed to undesirable temperatures;
   (b) moving the growth media comprising organisms from the holding tank to the PBR array to expose the growth media to growth conditions;
   (c) moving water from the water storage tank to the first heat exchanger to prevent the growth media comprising organisms from being exposed to undesirable temperatures; and
   (d) moving water from the water storage tank to the second heat exchanger array disposed outdoors and regulating the temperature of water in the water storage tank by heat exchange with ambient outdoor temperature.

7. The apparatus of claim 6 wherein the control system is configured to move water from the water storage tank to the first heat exchanger based on the temperature difference between the water storage tank temperature and holding tank temperature.

8. The apparatus of claim 7 further comprising at least one first sensor element to evaluate a harvestability status of the phototropic organisms in the growth medium wherein the control system is configured to automatically remove growth medium from at least one of the PBR array and the holding tank for harvesting based the evaluated harvestability status.

9. The apparatus of claim 7, further comprising a brine-based disinfectant system for disinfecting the PBR array after removing the growth medium for harvesting.

10. The apparatus of claim 8 wherein the first sensor element comprises at least one of ultraviolet spectrometers, infrared spectrometers, turbidity meters, particle counters, and nephelometers.

11. The apparatus of claim 8 wherein the harvestability status is biomass density of the growth media comprising organisms.

12. The apparatus of claim 7 further comprising at least one second second sensor element to determine if additional nutrients are required to be added to the holding tank.

13. The apparatus of claim 12 wherein the second sensor element comprises at least one of a $CO_2$ sensor, pH sensor, fixed nitrogen sensor, and a phosphate sensor.

14. A method for cultivating phototropic organisms, the method comprising:
(a) providing an apparatus as in claim 1;
(b) providing a colonized growth medium comprising a colony of phototropic organisms in a growth medium capable of supporting population growth of the colony;
(c) introducing the colonized growth medium into the PBR;
(d) monitoring temperature conditions in the PBR, and;
(e) using the control system to perform at least one of the following functions:
(i) moving the colonized growth medium from the PBR into the holding volume to prevent colonized growth medium in the PBR from being exposed to non-optimal temperatures; and
(ii) moving the colonized growth medium from the holding volume into the PBR to expose the colonized growth medium in the PBR to growth conditions;
(iii) moving heat transfer fluid in the heat transfer fluid holding volume to the first heat exchanger to expose heat transfer fluid to the ambient temperature;
(iv) moving heat transfer fluid in the heat transfer holding volume to the temperature control element connected to the growth medium holding volume.

15. The method of claim 14, wherein the step of moving the colonized growth medium from the PBR into the holding volume to prevent colonized growth medium in the PBR from being exposed to non-optimal temperatures comprises the steps of:
(a) determining a flow rate between the PBR and the holding volume that will achieve predetermined desirable thermal conditions in the PBR; and
(b) circulating the colonized growth medium between the PBR and the holding volume at the flow rate so determined.

16. The method of claim 14, wherein the step of moving the colonized growth medium from the PBR into the holding volume to prevent colonized growth medium in the PBR from being exposed to non-optimal temperatures comprises the step of removing substantially all of the colonized growth medium from the PBR.

17. The method of claim 16, further comprising the steps of:
(a) monitoring the colonized growth medium in for indications that the colony is ready for harvesting; and
(b) automatically removing the colonized growth medium from at least one of the PBR and the holding volume for harvesting.

18. The method of claim 14, further comprising the step of automatically disinfecting the PBR and the holding volume after removing the colonized growth medium for harvesting.

19. The method of claim 18, wherein the step of automatically disinfecting the PBR and the holding volume after removing the colonized growth medium for harvesting comprises using a chlorine based disinfectant solution generated on site using brine and electricity.

20. An apparatus for cultivating phototropic organisms in a growth media without the use of solar concentrators, the apparatus comprising:
a photo-bioreactor (PBR) array comprising plastic tubing and disposed outdoors through which growth media comprising organisms is circulated using a first pump while the PBR array is exposed to sunlight;
a holding tank for growth media comprising organisms disposed indoors and in fluid communication with the PBR array and the first pump and configured to receive the growth media comprising organisms from the PBR array;
a first heat exchanger disposed inside the holding tank through which a thermal energy storage fluid is circulated using a second pump to regulate the temperature of the growth media comprising organisms;
a thermal energy storage fluid tank disposed indoors and in fluid communication with the first heat exchanger;
a second heat exchanger array disposed outdoors through which thermal energy storage fluid from the thermal energy storage fluid tank is circulated using a third pump to regulate the temperature of thermal energy storage fluid in the storage tank by heat exchange with ambient outdoor air; and,
a control system configured to move thermal energy storage fluid from the thermal energy storage fluid storage tank to the first heat exchanger based on the temperature difference between the thermal energy storage fluid tank temperature and holding tank temperature, wherein the growth media holding tank volume is greater than the volume of the PBR array.

21. The apparatus of claim 20 wherein the thermal energy storage fluid is at least one of water, chlorinated water, and oil.

22. The apparatus of claim 20 wherein the phototropic organisms comprises at least one of *Spirulina* spp. and *Nannochloropsis* spp.

23. The apparatus of claim 20 wherein the temperature of the growth media comprising organisms is regulated to not exceed 38° C.

* * * * *